United States Patent
Hobbs et al.

(10) Patent No.: US 9,541,544 B1
(45) Date of Patent: Jan. 10, 2017

(54) METHOD OF SELECTING CHEMOTHERAPEUTIC AGENTS FOR AN ISOLATED ORGAN OR REGIONAL THERAPY

(71) Applicant: Delcath Systems, Inc., Queensbury, NY (US)

(72) Inventors: Eamonn P. Hobbs, Cleverdale, NY (US); Daniel S. Johnston, Trappe, PA (US)

(73) Assignee: Delcath Systems, Inc., New York, NY (US)

( * ) Notice: Subject to any disclaimer, the term of this patent is extended or adjusted under 35 U.S.C. 154(b) by 0 days.

(21) Appl. No.: 14/013,005

(22) Filed: Aug. 28, 2013

Related U.S. Application Data

(60) Provisional application No. 61/694,143, filed on Aug. 28, 2012.

(51) Int. Cl.
*G01N 33/50* (2006.01)

(52) U.S. Cl.
CPC .................. *G01N 33/5011* (2013.01)

(58) Field of Classification Search
CPC .................................... G01N 33/5011
USPC ............................................ 424/9.2; 435/32
See application file for complete search history.

(56) References Cited

U.S. PATENT DOCUMENTS 5,069,662 A * 12/1991 Bodden ................... 604/5.01

OTHER PUBLICATIONS

Alley et al., Feasibility of drug screening with panels of human tumor cell lines using a microculture tetrazolium assay. Cancer Research, vol. 48 (Feb. 1, 1988) pp. 589-601.*
Winchester et al., Will hemoperfusion be useful for cancer chemotherapeutic drug removal? Clinical Toxicology, vol. 17, No. 4 (1980) pp. 557-569.*
Bartlett et al., Isolated hepatic perfusion for unresectable hepatic metastases from colorectal cancer. Surgery, vol. 129, No. 2 (2000) pp. 176-187.*
Furukawa et al ., In vitro chemosensitivity of hepatocellular carcinoma for hepatic arterial infusion chemotherapy using the MTT assau with the combinations of antitumor drugs. Kurume Medical Journal, vol. 51 (2004) pp. 25-33.*

* cited by examiner

*Primary Examiner* — Kara Johnson
(74) *Attorney, Agent, or Firm* — Morgan, Lewis & Bockius LLP

(57) ABSTRACT

A method for optimal selection of cytotoxic agents for organ or region specific therapy that includes extracorporeal filtration of the cytotoxic agent from blood drained from the organ or region being treated and return of the filtered blood to a mammal is disclosed.

30 Claims, No Drawings

METHOD OF SELECTING CHEMOTHERAPEUTIC AGENTS FOR AN ISOLATED ORGAN OR REGIONAL THERAPY

CROSS-REFERENCE TO RELATED APPLICATIONS

This application claims priority benefit of U.S. Provisional Patent Application Ser. No. 61/694,143 filed Aug. 28, 2012, and entitled "A Method for Optimal Selection of Cytotoxic Agents for an Organ or Region Specific Therapy That Includes Extracorporeal Filtration of the Cytotoxic Agent." The disclosure of the aforementioned Provisional Patent Application Ser. No. 61/694,143 is hereby incorporated by reference in its entirety.

BACKGROUND

Worldwide, millions die of various cancers each year. In the United States, cancer remains the second most common cause of death. Developing effective treatments of proliferative disorders such as cancer is a continuing goal of the medical community. Systemic chemotherapy has provided limited effectiveness. One approach to treating cancer that is localized in an organ or region is to isolate that organ or region and provide a high dose of chemotherapy to that isolated organ or region. Regionalized and isolated organ (organ-specific) methods for chemotherapeutic treatment in conjunction with filtration of chemotherapeutic agents from blood and returning the filtered blood to a patient has been used to limit systemic toxicity and allow for high local drug concentrations at the site of disease.

SUMMARY

We have recognized that a limitation of regionalized and isolated organ methods for treating cancer has been the pairing of chemotherapeutic agents that are effective at treating the cancers of a region or organ with an effective filtration method to remove the chemotherapeutic agent from the blood before returning blood to the patient undergoing treatment. High efficiency filtration, or high filter efficiency, enables the use of high local drug concentrations at the site of disease where such concentrations of drugs if they entered the systemic system would be dangerous for patients. The effectiveness of the filtration of the chemotherapeutic agent limits systemic toxicity in this treatment approach. Filtration enables the use of chemotherapeutic agents that might not otherwise be available for treatment due to their toxicity but that can be highly effective at treating a cancer at a localized region or organ. Methods that combine treating an isolated organ, or region, with a chemotherapeutic agent, filtering the blood that drains from the organ, or region, to remove the chemotherapeutic agent from the blood, and returning the filtered blood to the patient have been effective at treating cancers but there is a need for establishing chemotherapeutic agent filtration system pairs that are useful in these methods.

Achieving more highly effective chemotherapeutic agents for a particular cancer along with establishing highly efficient filtration of those agents from blood where blood components are maintained after filtration would provide greatly improved therapeutic outcomes. Our approach meets the need for methods to optimize the pairing of chemotherapeutic agents with efficient, and safe, filtration of the chemotherapeutic agents from blood by testing the chemotherapeutic agents for effectiveness in killing cancer cells and establishing filter conditions that remove the chemotherapeutic agents from blood while maintaining the viability of the blood. Maintaining the viability of the blood generally means that blood components are not reduced to levels that are clinically unacceptable. By testing the chemotherapeutic agents with different cancer cell lines and establishing safe and effective filtration of the effective chemotherapeutic agents the method provided herein, in some embodiments, enables the pairing of chemotherapeutic agents with filters useful for those agents so that effective regionalized or isolated organ chemotherapy can be achieved. Alternatively, effective chemotherapeutic agents can be paired with filters useful in removing them from blood by varying filter parameters with a particular chemotherapeutic agent until optimal filter efficiency is maintained under conditions where the blood viability is maintained.

Improving the chemotherapeutic agent options in isolated organ or regional therapy (also referred to as regionalized therapy) will greatly enhance treatment options. Accordingly, we have solved this problem by providing methods, in some embodiments, of selecting chemotherapeutic agents for isolated organ or regional therapy and pairing those chemotherapeutic agents with filters capable of removing the chemotherapeutic agents from blood with high efficiency.

In some embodiments, provided is a method for identifying one or more pharmaceutical agents, drugs, suitable for use in a system of percutaneous organ or regional arterial infusion of cytotoxic agent coupled with collection of venous organ or regional outflow and extracorporeal filtration.

In some embodiments, provided is a method of selecting chemotherapeutic agents for use in a regional or an isolated organ treatment of a cancer in a mammal where the chemotherapeutic agent is filtered from blood and returned to the mammal, comprising screening chemotherapeutic agents for effectiveness against the cancer and identifying chemotherapeutic agents capable of being filtered from blood at a rate of flow of from about 100 to about 1000 mL/minute. In some embodiments the chemotherapeutic agents capable of being filtered from blood are filtered with high efficiency. In some embodiments, screening chemotherapeutic agents comprises cancer cell line screens to determine effectiveness in killing cells of cancer cell lines. In some embodiments, the cancer cell lines are of multiple origins. In some embodiments cell line screens comprise short term exposure to the chemotherapeutic agent. In some embodiments, short term exposure is a length of time from about 30 minutes to about 2 hours. In some embodiments, the screening comprises reviewing data previously available and in some embodiments, the screening comprises determining effectiveness in shrinking tumor size In some embodiments identifying chemotherapeutic agents capable of being filtered from blood comprises in vitro assays of filter efficiency. In some embodiments identifying chemotherapeutic agents cable of being filtered from blood comprises in vivo screens in a mammal to determine filter efficiency. In some embodiments, identifying chemotherapeutic agents capable of being filtered from blood further comprises establishing that the filter does not substantially remove blood components. In some embodiments, the mammal is selected from cat, dog, rodent, pig, horse, goat sheep and human.

In some embodiments, provided is a method of selecting chemotherapeutic agents for use in a regional or an isolated organ treatment of a cancer in a patient where blood is filtered to remove the chemotherapeutic agent before the blood is returned to the patient, comprising: screening chemotherapeutic agents for effectiveness against the cancer by establishing that it can kill cancer cells of the type of the cancer; identifying chemotherapeutic agents that can be filtered from blood with high efficiency, wherein a chemotherapeutic agent that is effective against the cancer and capable of being filtered from blood with high efficiency can be used in the regional or the isolated organ treatment. In some embodiments, the isolated organ treatment is percutaneous hepatic perfusion. In some embodiments, the method further comprises establishing an effective dose for killing the cancer cell.

In some embodiments, provided is a method of optimizing selection of chemotherapeutic agents for use in an isolated region or isolated organ treatment of a cancer in a mammal where blood is filtered to remove the chemotherapeutic agent before the blood is returned to the mammal, comprising identifying a chemotherapeutic agent effective at treating the cancer at high dose and short term exposure by testing through a dose range of 0 to 20 times the maximal tolerated system concentration, determining a filtration media that can adsorb the chemotherapeutic agent from blood at flow rates of about 100 to about 1000 mL/minute, and establishing that the chemotherapeutic agent at effective doses for killing cancer is not toxic to the region or organ being treated. In some embodiments, short term exposure comprises between about 30 to about 120 minutes. In some embodiments, identifying a chemotherapeutic agent effective at treating the cancer comprises determining effectiveness at killing cancer cells of the cancer. In some embodiments, determining effectiveness at killing cancer cells of the cancer comprises screening cancer cell lines of one or more cancer types. In some embodiments, determining effectiveness at killing cancer cells of the cancer comprises reviewing clinical or pre-clinical data. In some embodiments, identifying a chemotherapeutic agent effective at treating the cancer by determining effectiveness at treating multiple cell lines with a chemotherapeutic agent of interest to identify which cell type the chemotherapeutic agent is effective at killing by establishing $EC_{50}$ values or concentrations for inducing apoptosis as less than or equal to chemotherapeutic agents established to be effective. In some embodiments, determining a filtration media that can adsorb the chemotherapeutic agent from blood comprises varying filtration media parameters to achieve high efficiency filtration. In some embodiments, the filtration media is an activated carbon media. In some embodiments, where the filtration media is an activated carbon, determining a filtration media that can adsorb the chemotherapeutic agent from blood comprises varying parameters of the activated carbon selected from density, pore volume, surface area, pore size and combinations thereof.

In some embodiments, provided is a method of optimizing selection of chemotherapeutic agents for use in an isolated region or isolated organ treatment of a cancer in a mammal where blood is filtered to remove the chemotherapeutic agent before the blood is returned to the mammal, comprising identifying a chemotherapeutic agent effective at treating the cancer by determining effectiveness at killing cancer cell lines, determining a filtration media that can adsorb the chemotherapeutic agent from blood at flow rates of about 100 to about 1000 mL/minute, and establishing that the chemotherapeutic agent at effective doses for killing cancer is not toxic to the region or organ being treated. In some embodiments, the isolated organ treatment is percutaneous hepatic perfusion.

In some embodiments, provided is a method identifying chemotherapeutic agents for use in regional or isolated organ treatment of a cancer, comprising identifying chemotherapeutic agents suitable for killing cancer cells of interest in a short term treatment of between 30 and 120 minutes at doses that will not cause irreversible toxicity to the organ or region being treated and developing a filtration system capable of filtering the chemotherapeutic agents at high efficiency from whole blood or plasma at flow rates of between about 100 mL/minute to about 1000 mL/minute.

DETAILED DESCRIPTION

Provided, in various embodiments, are methods for identifying effective chemotherapeutic agents for a particular cancer useful in regionalized or isolated organ treatments and pairing this identification with establishing that these chemotherapeutic agents can be filtered from blood with high efficiency and maintenance of blood components. These methods can provide greatly improved therapeutic outcomes by establishing the most effective chemotherapeutic agents that can be used in isolated organ or regional cancer therapies.

In some embodiments the method disclosed herein comprises the steps of identifying an organ or region for treatment, identifying cancer types that occur or metastasize to the organ or region, establishing a panel of candidate chemotherapeutic agents, screening the panel of candidate chemotherapeutic agents with cancer cell lines for their capacity to induce cell death of the cancer cell lines; determining the toxicity of the cytotoxic agents in the organ or region of treatment; and establishing a method of efficiently filtering the cytotoxic agent from blood.

In some embodiments, screening comprises using a series of concentrations of cytotoxic agents to determine the lowest concentration that induces apoptosis in each of the cell lines.

In some embodiments, the screening establishes the dose in which 90% of the cells do not survive. In some embodiments, the screening establishes the dose in which 50% of the cells do not survive, i.e., $EC_{50}$.

In screening chemotherapeutic agents for effectiveness in treating cancer, cancer cell lines can be used. Effectiveness in treating cancer can be determined by establishing an $EC_{50}$ for the chemotherapeutic agents test for each chemotherapeutic agent within the understanding of persons of skill in art. In some embodiments, the person of skill in the art will work to find chemotherapeutic agents that have a low $EC_{50}$ for primary cancer cells, or cell lines, and a high $EC_{50}$ for the organ, or cells of the organ, or region, to be treated with the chemotherapeutic agent. This step can be used to establish optimal chemotherapeutic agents from a biological perspective. Combining this approach with identification of filter media that enable efficient filtration of the chemotherapeutic agents establishes chemotherapeutic agents useful in regionalized or isolated organ treatments.

In some embodiments, screening comprises determining effectiveness in shrinking tumor size. This can be done in animal models where during an organ, or region, treatment procedure, with changes in tumor size monitored post procedure. In addition, 3-dimensional in vitro cultures could be used to mimic tumors in this screening. These methods are understood by persons of skill in the art.

Determining the toxicity of the cytotoxic agents in the organ or region of treatment can comprise in some embodiments, evaluation of markers of cytotoxicity such as, for example, apoptosis, mitochondrial membrane stability, increases in reactive oxygen species. In some embodiments, the cells used to evaluate the toxicity of the cytotoxic agent in the organ or region would be cells that predominate in the organ or region. For example, in the liver the cells that would be evaluated for the cytotoxic agent's toxicity would be hepatocytes. In some embodiments, the method optimizes the toxicity of the cytotoxic agents to target cancer cells while at the same time minimizing toxicity to the cells of the organ being treated. In some embodiments, the method optimizes the toxicity of the cytotoxic agents to target cancer cells while at the same time minimizing toxicity to the cells of the organ being treated, and optimizing the ability to filter the cytotoxic agent from the blood.

In some embodiments blood is analyzed in an in vitro system after passing through a filter with a media of interest. In some embodiments, blood is monitored in the circulation of an animal to determine if blood components have been changed after passing through a filter with a media of interest. Blood components can be measured in blood or plasma. In some embodiments, blood components are measured pre and post filtration and per pass extraction monitored over time.

Blood components such as albumin, platelets, and neutrophils can be determined before and after filtration in the methods described herein at the flow rates used in the isolated organ treatment to establish that a significant amount of blood components is not adsorbed by the filter. In establishing a filter media useful in accordance with some embodiments of the invention, the blood components albumin, platelets, and neutrophils can be measure to be established that these components are not removed to an extent that the blood would be damaged in accordance with clinical guideline understood by persons of skill in the art.

In some embodiments, identifying chemotherapeutic agents capable of being filtered comprises establishing that the filter does not substantially remove blood components. Blood components include, for example, platelets, white blood cells, albumin, globulin, and fibrinogen. As used herein, the term "does not substantially remove blood components" means that less than 80% of platelets, less than about 50% for white blood cells, less than about 60% for albumin, less than about 55% for globulin, and less than about 60% for fibrinogen are removed from blood by the filter.

Filter efficiency is determined in accordance with the equation.

$$\text{Filter efficiency} = ((C_{\text{pre-filter}} - C_{\text{post-filter}})/C_{\text{pre-filter}}) \times 100$$

The term "high efficiency" as used herein with respect to chemotherapeutic agents being filtered from blood means, in some embodiments, at least about 70%. In some embodiments, high efficiency means at least about 80%. In some embodiments, high efficiency means at least about 85%. In some embodiments, high efficiency means at least about 90%. In some embodiments, high efficiency means at least about 95%. In some embodiments, high efficiency means at least about 98%. In some embodiments, high efficiency means at least about 99%. As used herein, the terms "high efficiency" and "high filter efficiency" and "efficiently filtering" are used interchangeably and refer to the filter efficiency as determined by the above recited equation.

The cytotoxic agent, as used herein, can refer to an agent that kills cells in any disease relating to abnormal cell growth, such as, for example, a cancer. Short term, as used herein, means the treatment, in some embodiments will take less than two hours, in some embodiments, the treatment will take less than 90 minutes, in some embodiments the treatment will take 60 minutes or less, in some embodiments the treatment will take 30 minutes or less.

In some embodiments, the method or system identifies organs or regions of interest for treatment, identifies cancer types that occur or metastasize to the organ or region, and identifies cytotoxic agents that induce cell death and can be filtered from the blood.

In some embodiments, disclosed herein is a method or system for selecting cytotoxic agents for short term targeted therapy of local organs or regions in a percutaneous administration of one or more cytotoxic agents to specific body organ or regions of a patient with subsequent extracorporeal filtration of the blood laden with cytotoxic agent drained from the organ or region after treatment to remove the cytotoxic agent from the blood and then return of the filtered blood to the patient. In some embodiments the cytotoxic agent is administered intra-arterially and the blood drained from the organ or region is venous blood.

In some embodiments, cytotoxic agents include agents that can induce the death of cells harmful to an organ or region being treated. Cytotoxic agents include, for example, chemotherapeutic agents, or anti-proliferative agents, useful for killing cancer cells.

In some embodiments, short term targeted therapy of local organs or regions relates to a therapy that takes less than two hours. In some embodiments, short term targeted therapy of local organs or regions relates to a therapy that takes 120 minutes or less. In some embodiments, short term targeted therapy of local organs or regions relates to a therapy that takes 90 minutes or less. In some embodiments, short term targeted therapy of local organs or regions relates to a therapy that takes 60 minutes or less. In some embodiments, short term targeted therapy of local organs or regions relates to a therapy that takes 30 minutes or less.

In some embodiments efficacy and toxicity screening can be done in live mammals.

In some embodiments the patient or subject is a mammal. In some embodiments the mammal is a cat, dog, rodent, pig, cow, horse, sheep or goat. In some embodiments the mammal is a human.

In some embodiments of the invention, the method disclosed herein is used to provide small molecule agents, compounds, that can be used with a percutaneous hepatic perfusion (PHP) system for use in the arterial delivery of a small molecule chemotherapy agent such as melphalan to the liver, with subsequent filtration of the drug after it passes through the liver and before it enters the systemic circulation, in order to reduce potential systemic toxicity. Such a system is described, for example, in U.S. Pat. No. 5,069,662 to Bodden, which is herein incorporated by reference. The Delcath PHP System Kit, for example, utilizes a series of catheters and filters to target drug delivery to the liver and to filter it out before it reaches systemic circulation.

A variety of test media that can be used with different embodiments of the invention. For example, a hydrogel coated activated carbon that has a porous structure is effective in removing organic compound chemotherapy agents from blood. Various parameters can be changed such as density, pore size, and surface area of the activated carbon to achieve optimal filtration of particular chemotherapeutic agents from blood. In some embodiments, a single chemotherapeutic agent can be tested with filters with parameters varied to determine a filter with an optimal efficiency for that chemotherapeutic agent In some embodiments, chemotherapeutic agents are tested with a panel of cancer cell lines. Cytotoxicity of different chemotherapeutic agents is tested for different cancer cell lines to determine which chemotherapeutic agents are effective in treating different cancer types. Once a chemotherapeutic agent is selected, in some embodiments, filter media and filter conditions can than be varied to determine a filter that will have an optimal efficiency at removing the chemotherapeutic agent from blood.

In some embodiments, chemotherapeutic agents are first selected to determine chemotherapeutic agents that will have minimal toxicity to the cells of the organ or region that do not bear cancer.

While various embodiments of the invention can be used to evaluate any effective chemotherapeutic agent, chemotherapeutic agents that would not be useful systemically because of their toxicity profile can now be useful due to their filtration from the blood. Compounds that have not been used because of their toxicity can be used if, in accordance with methods disclosed herein, they can be shown to be effective at causing cell death of cancer cells that are targeted and that they can also be efficiently filtered from blood that has been removed from the organ or region being treated.

The selection of a drug for use as a chemotherapeutic in a regional or isolated organ treatment is determined by evaluating in some embodiments the ability to kill tumor cells, toxicity on the organ or region to be treated, and the ability to filter the drug. For example, if toxicity in the organ/region to be treated is shown to occur at 1.0 ug cytotoxic agent/mg of tissue, but effective cancer cell killing occurs at 0.25 ug of cytotoxic agent/mg of tumor, then there would be a 4-fold dose range where killing would be expected and toxicity would not. If multiple chemotherapeutic agents are tested, a rank order can be made to establish the most useful chemotherapeutic agents for a particular system.

The choice of chemotherapeutic agent for a particular system involves, in some embodiments, identifying a chemotherapeutic agent/dose with the optimal/maximal difference between effective cancer cell killing versus inducing cytotoxicity to the organ/region while also having a filtration efficiency sufficient to prevent extra-organ or extra-regional plasma concentrations that can cause clinically unmanageable toxicity in those areas.

In some embodiments, the method of the invention achieves optimized therapy by considering the following parameters to be optimized, establish minimal or clinically manageable toxicity of treated organ or region within effective dose/treatment parameters, induce cancer cell death within dose time treatment parameters, and establish filter efficiency to minimize or prohibit systemic toxicities.

In some embodiments, chemotherapeutic agents that could be screened with the methods disclosed herein include, for example, melphalan, doxorubicin (also known as hydroxydaunorubicin and sold under the brand names Adriamycin, Adriamycin PFS, Adriamycin RDF, or Rubex), Docetaxel, paclitaxel, fluorinated pyrimidines (5-fluorouracyl 5-FU or floxuridine FURD), cisplatin, oxaliplatin, topotecan. Mytomycin C, cyclophosphamide, methotrexate, vincristine, Bleomycin, FAMT, pharmaceutically acceptable salts thereof, combinations thereof, and other such compounds known to persons of skill in the art.

In some embodiments, chemotherapeutic agents that could be tested include, but are not limited to, cisplatin, denopterin, edatrexate, methotrexate, nolatrexed, pemetrexed, piritrexim, pteropterin, raltitrexed, trimetrexate, cladribine, clofarabine, fludarabine, 6-mercaptopurine, nelarabine, thiamiprine, thioguanine, tiazofurin, ancitabine, azacitidine, 6-azauridine, capecitabine, carmofur, cytarabine, decitabine, doxifluridine, enocitabine, floxuridine, fluorouracil, gemcitabine, tegafur, troxacitabine, pentostatin, hydroxyurea, cytosine arabinoside, docetaxel, paclitaxel, abraxane, topotecan, adriamycin, etoposide, fluorouracil (5-FU), and cyclophosphamide. In one embodiment, the agent can be selected from platinum-based chemotherapeutic agents (e.g., cisplatin), alkylating agents (e.g., nitrogen mustards), antimetabolites (e.g., pyrimidine analogs), radioactive isotopes (e.g., phosphorous and iodine), miscellaneous agents (e.g., substituted ureas) and natural products (e.g., *vinca* alkyloids and antibiotics). In another embodiment, the therapeutic agent can be selected from the group consisting of allopurinol sodium, dolasetron mesylate, pamidronate disodium, etidronate, fluconazole, epoetin alfa, levamisole HeL, amifostine, granisetron HCL, leucovorin calcium, sargramostim, dronabinol, mesna, filgrastim, pilocarpine HCl, octreotide acetate, dexrazoxane, ondansetron HCL, ondanselron, busulfan, carboplatin, cisplatin, thiotepa, melphalan HCl, melphalan, cyclophosphamide, ifosfamide, chlorambucil, mechlorethamine HCL, carmustine, lomustine, polifeprosan 20 with carmustine implant, streptozocin, doxorubicin HCL, bleomycin sulfate, daunirubicin HCL, dactinomycin, daunorucbicin citrate, idarubicin HCL, pllmycin, mitomycin, pentostatin, mitoxantrone, valrubicin, cytarabine, tludarabine phosphate, floxuridine, cladribine, methotrexate, mercaptipurine, thioguanine, capecitabine, methyltestosterone, nilutamide, testolactone, bicalutamide, flutamide, anastrozole, toremifene citrate, estramustine phosphate sodium, ethinyl estradiol, estradiol, esterified estrogens, conjugated estrogens, leuprolide acetate, goserelin acetate, medroxyprogesterone acetate, megestrol acetate, levamisole HCL, aldesleukin, irinotecan HCL, dacarbazine, asparaginase, etoposide phosphate, gemcitabine HCL, altretamine, topotecan HCL, hydroxyurea, interferon alpha-2b, mitotane, procarbazine HCL, vinorelbine tartrate, *E. coli* 1-asparaginase, *Erwinia* L-asparaginase, vincristine sulfate, denileukin diftitox, aldesleukin, rituximab, interferon alpha-1a, paclitaxel, abraxane, docetaxel, BCG live (intravesical), vinblastine sulfate, etoposide, tretinoin, teniposide, porfuner sodium, tluorouracil, betamethasone sodium phosphate and betamethasone acetate, letrozole, etoposide citrororum factor, folinic acid, calcium leucouorin, 5-fluorouricil, adriamycin, c}toxan, and diaminodichloro-platinum.

In some embodiments, pharmaceutically acceptable salts of any of the chemotherapeutic agents disclosed herein are used. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of melphalan, paclitaxel, and oxaliplatin can be prepared from an inorganic acid or from an organic acid. Inorganic acids include, for example, hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxyethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, ?-hydroxybutyric, salicylic, galactaric and galacturonic acid. Pharmaceutically-acceptable base addition salts include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound.

Filter cartridge tubes used in some embodiments can be of any biologically compatible material. For example, the filter cartridge tube, filter cartridge top, and filter cartridge bottom can be made of a polycarbonate, a polysulfone, an acrylic, and the like. Where the filter apparatus will be used for blood filtration the filter cartridge tube and filter cartridge top and bottom should be made of a hemo-compatible material such as thermoplastics or thermosetting plastics. Such plastics include, for example, polycarbonates, polysulfones, acrylic, polyethylene, polypropylene, polyester, nylon, polycarbonate, and the like. The material may be transparent or opaque, although materials that are at least partially transparent offer some advantages in that the purging of bubbles from the filter media can be easily visualized.

In some embodiments, a filter media for removing toxic compounds from a biological fluid is used. In some embodiments, a filter media used in blood detoxification, or purification is used. In some embodiments, the filter media is a carbon, or activated carbon, based adsorbent material. In some embodiments, the filter media extracts or removes toxic compounds from blood. In some embodiments the filter media for extracting toxic compounds is a carbon based adsorbent material coated with a biocompatible synthetic, natural or chemical coating or modification, that can render the carbon based adsorbent material hemo-compatible while at the same time maintaining the adsorbent capacity of the carbon-based adsorbent. Such coatings include, for example, methacrylates. In some embodiments, the filter media is made up of polymer coated activated carbon cores, for example, granules or spheres coated with a polymer coat to render them cores hemo-compatible.

In some embodiments, the carbon cores have a diameter of from about 0.45 mm to about 1.15 mm. In some embodiments of the invention the carbon cores have an average diameter of about 0.73 mm. Various parameters can be changed in order to establish optimal filtration for a particular chemotherapeutic agent.

A variety of polymer coated carbon cores are coated with a semipermeable polymer coating comprised of material selected from cellulose, a methacrylate polymer, and combinations thereof. In some embodiments of the invention the polymer coating is selected from the group consisting of polymethylmethacrylate (PMMA), polyethylmethacrylate (PEMA), polyhydroxyethyl-methacrylate (PHEMA) and combinations thereof.

The coating that surrounds the carbon cores in some embodiments is comprised of poly(2-hydroxyethyl methacrylate). The thickness of the coating that covers the particles is determined largely by the mass ratio of carbon cores to poly(2-hydroxyethyl methacrylate) used in the coating process.

EXAMPLES

Example 1

Filter Efficiency for Different Chemotherapeutic Agents

A small scale hemofiltration cartridge of about 93 mL was filled with a hemocompatible carbon based media to compare the efficiency of a filter in removing different chemotherapeutic agents. The extracorporeal circuit was modified to contain 40% of the internal volume of a Delcath circuit and connected to the cartridge. The filter and circuit were primed, and a 1 liter bag of bovine blood was connected to the circuit inlet and outlet lines. Blood was circulated at 100 mL/min using a Medtronic Bioconsole 560. Chemotherapeutic agents (drugs) were then infused downstream of the blood source and upstream of the filter cartridge. The chemotherapeutic agents (drugs) were infused at a constant flow rate over a 30 minute time period at doses shown in Table 1 using a syringe pump. Blood samples were collected every 5 minutes at ports immediately before and after the filter cartridge. Samples were then centrifuged and plasma aliquots were analyzed by LC/MS/MS for chemotherapeutic agent (drug) concentrations.

TABLE I

| Drug (powder) | Dose (mg) | Solution |
| --- | --- | --- |
| Melphalan | 44 | 11.7 µL Hydrochloric Acid, 4.4 mL methanol, 91.6 mL 0.9% saline |
| Idarubicin | 40 | 2.1 mL methanol, 93.9 mL 0.9% saline |
| Paclitaxel | 90 | 7.6 mL Cremaphor EL, 7.6 mL ethanol, 80.8 mL 0.9% saline |
| Doxorubicin | 60 | 2.1 mL methanol, 93.9 mL 0.9% saline |
| Carboplatin | 150 | 1.07 mL water, 85.3 mL 0.9% saline |
| Gemcitabine | 500 | 96 mL 0.9% saline |

Filter efficiencies at different time points calculated according to:

$$((C\text{pre-filter} - C\text{post-filter})/C\text{pre-filter}) \times 100$$

TABLE II

| Time | Melphalan | Idarubicin | Paclitaxel | Doxorubicin | Carboplatin | Gemcitabine |
| --- | --- | --- | --- | --- | --- | --- |
| 5 | 99.67 | 75.43 | 62.39 | 98.52 | 98.96 | 98.61 |
| 10 | 98.59 | 67.00 | 38.53 | 97.78 | 97.81 | 99.68 |
| 15 | 97.86 | 58.59 | 42.74 | 97.68 | 97.54 | 99.36 |
| 20 | 97.63 | 52.69 | 21.26 | 97.19 | 97.55 | 99.42 |
| 25 | 97.39 | 48.06 | 34.66 | 96.36 | 97.43 | 99.42 |
| 30 | 97.04 | 51.02 | — | 96.47 | 95.95 | 98.98 |
| Average | 98.03 | 58.80 | 39.92 | 97.33 | 97.54 | 99.25 |

TABLE III

Filter Efficiencies with combinations of drugs

| Time | Combination Gemcitabine/Carboplatin (filter efficiency for Gemcitabine) | Combination Gemcitabine/Carboplatin (Filter efficiency for Carboplatin) |
|---|---|---|
| 5 | 99.92 | 99.92 |
| 10 | 99.93 | 99.61 |
| 15 | 99.86 | 98.85 |
| 20 | 99.70 | 97.44 |
| 25 | 99.73 | 97.09 |
| 30 | 99.26 | 93.23 |
| Average | 99.73 | 97.69 |

Evaluation of Cytotoxic Agent(s) Ability to Induce Cancer Cell Death

Following Short Term Exposure

In Vitro:

A panel of cancer cell lines (for example, 5-500 cell lines) can be analyzed with a drug of interest via a dose response for a duration consistent with the expected exposure of the drug in a clinical procedure. For example, if organ/regional treatment is expected to be 1 hour, then cell dosing can be for approximately one hour. After dosing the media is removed, washed with media that does not contain cytotoxic agent, add media without cytotoxic agent and continue to culture until time that parameters need to be evaluated according to protocol. Parameters to be measure can include, but are not limited to, induction of apoptosis such as, for example, by evaluating Caspase 3 activity or Caspase 3 phosphorylation, determining cell number, using for example a nuclear dye such as DAPI, or determining cell viability by measuring ATP or other determinant known to persons of skill in the art.

In Vivo:

A method for evaluating short term dosing as a means to effectively kill cancer cells is to use whole animal systems to evaluate the death of induced or spontaneous tumors in an organ-specific, regional or whole animal system. Tumors can be formed by natural progression in normal animals, induction via administration of carcinogenic agents, injection of defined or undefined cancerous cells into immuno-suppressed animal models, or via natural progression from genetically modified animals. Various measures can be used to determine effects, such as determining apoptosis, comparative volumetric imaging of solid tumors pre and post procedure, measurement of longest side of surface tumors pre and post treatment. Also, removal of solid tumors at defined times following whole animal, organ or region-specific administration with or without venous collection and extracorporeal filtration followed by isolation of RNA and protein and analysis of expression indicative of apoptosis and/or necrosis or presence of protein levels of protein modifications consistent with apoptosis or necrosis can be used.

Evaluation of Organ Toxicity Induced by Cytotoxic Agents

In Vitro

Cell line screens. In general human or animal cells can be plated from an organ of interest for a sufficient period of time to allow them to become stable and, if appropriate, adhered to a culture dish. Cultured human hepatocytes can be used to determine organ toxicity where the organ is the liver. Dosing can be for an amount of time mimicking expected exposure from a clinical procedure. Multiple doses are required and an $EC_{50}$ for toxicity can be calculated. Markers for toxicity should be able to be induced within the time frame of the experiment and a positive control should be used.

In Vivo

Organ specific toxicity can be accomplished using intact animals dosed systemically or with isolated systems where the cytotoxic agent is injected directly into the organ. Organ perfusion systems whereby organs are removed from the body and studied in situ (or the organ is left in the body but the vasculature is disconnected and the organ is perfused directly in the animal can be used. Toxicity in whole organ systems can be determined histologically, immunohistologically or by other means known to persons of skill in the art. Organs can be removed and portions used for protein or RNA analysis.

Evaluation of Filtration Efficiency

In Vitro

Filtration efficiency can be determined using a simulated in vitro filtration system designed to measure multiple parameters including filtration efficiency. The amount of drug (chemotherapeutic agent) in the blood at any time or location in the circuit can be performed by one of several methods, including but not limited, to HPLC and LC-MS/MS.

Filtration Efficiency is calculated according to((Pre Filter Concentration-Post Filter Concentration)/ (Pre Filter Concentration))×100

In Vivo

In vivo filter efficiency can be measured on a human or animal by utilizing a Percutaneous Intra-Arterial Administration system on a defined organ or region with subsequent extracorporeal filtration of the regional venous blood. The amount of drug (chemotherapeutic agent) in the blood at any time or location in the circuit can be performed by one of several methods, including but not limited, to HPLC and LC-MS/MS.

Filtration Efficiency is calculated according to((Pre Filter Concentration-Post Filter Concentration)/ (Pre Filter Concentration))×100

A number of embodiments have been described and are to be considered as illustrative and not restrictive. It will be understood that various modifications may be made without departing from the spirit and scope of the invention and that the claims should not be limited to the versions and embodiments described herein.

What is claimed is:

1. A method of identifying chemotherapeutic agents for use in a regional or an isolated organ treatment of a cancer in a mammal where the chemotherapeutic agent is filtered from blood and returned to the mammal, comprising:
    screening a panel of chemotherapeutic agents for effectiveness against the cancer;
    screening the panel of chemotherapeutic agents for toxicity in the organ to be treated; and
    identifying chemotherapeutic agents from the panel of chemotherapeutic agents that are capable of being filtered from blood at a rate of flow of from about 100 to about 1000 mL/minute.

2. The method of claim 1, wherein chemotherapeutic agents capable of being filtered from blood are filtered with an efficiency of at least about 70%.

3. The method of claim 1, wherein screening chemotherapeutic agents comprises cancer cell line screens to determine effectiveness in killing cells of cancer cell lines.

4. The method of claim 3, wherein cancer cell lines are of multiple origins.

5. The method of claim 3, wherein the cell line screens comprise short term exposure to the chemotherapeutic agent.

6. The method of claim 5, wherein the short term exposure is a length of time from about 30 minutes to about 2 hours.

7. The method of claim 1, wherein screening chemotherapeutic agents comprises reviewing data previously available.

8. The method of claim 1, wherein screening chemotherapeutic agents comprises determining effectiveness in shrinking tumor size.

9. The method of claim 1, wherein identifying chemotherapeutic agents capable of being filtered from blood comprises in vitro assays of filter efficiency.

10. The method of claim 1, wherein identifying chemotherapeutic agents cable of being filtered from blood comprises in vivo screens in a mammal to determine filter efficiency.

11. The method of claim 1, wherein identifying chemotherapeutic agents capable of being filtered from blood further comprises establishing that the filter does not substantially remove blood components.

12. The method of claim 1, wherein the mammal is selected from the group consisting of cat, dog, rodent, pig, cow, horse, goat, sheep and human.

13. The method of claim 1, wherein the mammal is a human.

14. A method of selecting chemotherapeutic agents for use in a regional or an isolated organ treatment of a cancer in a patient where blood is filtered to remove the chemotherapeutic agent before the blood is returned to the patient, comprising:
   screening a panel of chemotherapeutic agents for effectiveness against the cancer by establishing that it can kill cancer cells of the type of the cancer;
   screening the panel of chemotherapeutic agents for toxicity in the organ to be treated
   identifying chemotherapeutic agents that can be filtered from blood with an efficiency of at least about 70%; and
   selecting one or more of the chemotherapeutic agent that is effective against the cancer and capable of being filtered from blood with an efficiency of at least about 70% for use in the regional or the isolated organ treatment.

15. The method of claim 14, wherein the isolated organ treatment is percutaneous hepatic perfusion.

16. The method of claim 14, further comprising establishing an effective dose for killing the cancer cell.

17. A method of optimizing selection of chemotherapeutic agents for use in an isolated region or isolated organ treatment of a cancer in a mammal where blood is filtered to remove the chemotherapeutic agent before the blood is returned to the mammal, comprising:
   identifying a chemotherapeutic agent effective at treating the cancer at high dose and short term exposure by testing through a dose range of 0 to 20 times the maximal tolerated system concentration;
   determining a filtration media that can adsorb the chemotherapeutic agent from blood at an efficiency of at least about 70% and at flow rates of about 100 to about 1000 mL/minute and does not substantially remove blood components; and
   establishing that the chemotherapeutic agent at effective doses for killing cancer is not toxic to the region or organ.

18. The method of claim 17, wherein the short term exposure comprises between about 30 minutes to about 120 minutes.

19. The method of claim 17, wherein identifying a chemotherapeutic agent effective at treating the cancer comprises determining effectiveness at killing cancer cells of the cancer.

20. The method of claim 19, wherein determining effectiveness at killing cancer cells of the cancer comprises screening cancer cell lines of one or more cancer types.

21. The method of claim 17, wherein determining effectiveness at killing cancer cells of the cancer comprises reviewing clinical or pre-clinical data.

22. The method of claim 17, wherein identifying a chemotherapeutic agent effective at treating the cancer by determining effectiveness at treating multiple cell lines with a chemotherapeutic agent of interest to identify which cell type the chemotherapeutic agent is effective at killing by establishing a dose in which 50% of the cells do not survive (EC50) values or concentrations for inducing apoptosis as less than or equal to chemotherapeutic agents established to be effective.

23. The method of claim 17, wherein determining a filtration media that can adsorb the chemotherapeutic agent from blood comprises varying filtration media parameters to achieve filtration of an efficiency of at least about 70%.

24. The method of claim 23, wherein the filtration media is an activated carbon media.

25. The method of claim 24, wherein determining a filtration media that can adsorb the chemotherapeutic agent from blood comprises varying parameters of the activated carbon selected from density, pore volume, surface area, pore size and combinations thereof.

26. A method of optimizing selection of chemotherapeutic agents for use in an isolated region or isolated organ treatment of a cancer in a mammal where blood is filtered to remove the chemotherapeutic agent before the blood is returned to the mammal, comprising:
   identifying a chemotherapeutic agent effective at treating the cancer by determining effectiveness at killing cancer cell lines;
   determining a filtration media that can adsorb the chemotherapeutic agent from blood at an efficiency of at least about 70% and at flow rates of about 100 to about 1000 mL/minute and does not substantially remove blood components; and
   establishing that the chemotherapeutic agent at effective doses for killing cancer is not toxic to the region or organ.

27. The method of claim 26, wherein the organ is a liver.

28. A method of identifying chemotherapeutic agents for use in regional or isolated organ treatment of a cancer, comprising:
   identifying chemotherapeutic agents suitable for killing cancer cells of interest in a short term treatment of between 30 minutes and 60 minutes at doses that will not cause irreversible toxicity to a_region or an organ of the regional or isolated organ treatment; and
   developing a filtration system capable of filtering the chemotherapeutic agents at a filter efficiency of at least about 70% from whole blood or plasma at flow rates of between about 100 mL/minute to about 1000 mL/minute and does not substantially remove blood components.

29. The method of claim 28, wherein the filtration system comprises a filter media which comprises activated carbon.

30. The method of claim 29, wherein developing the filtration system further comprises varying parameters of the activated carbon wherein the parameters are selected from density, pore volume, surface area, pore size and combinations thereof.

* * * * *